US011170031B2

(12) United States Patent
Martin et al.

(10) Patent No.: US 11,170,031 B2
(45) Date of Patent: Nov. 9, 2021

(54) EXTRACTION AND NORMALIZATION OF MUTANT GENES FROM UNSTRUCTURED TEXT FOR COGNITIVE SEARCH AND ANALYTICS

(71) Applicant: INTERNATIONAL BUSINESS MACHINES CORPORATION, Armonk, NY (US)

(72) Inventors: Richard L. Martin, Jamaica Plain, MA (US); Antonio Jose Jimeno Yepes, Melbourne (AU); David Martinez Iraola, Sunnyvale, CA (US); Alix Lacoste, Brooklyn, NY (US); Christine Schieber, Southbank (AU)

(73) Assignee: International Business Machines Corporation, Armonk, NY (US)

( * ) Notice: Subject to any disclaimer, the term of this patent is extended or adjusted under 35 U.S.C. 154(b) by 347 days.

(21) Appl. No.: 16/119,480

(22) Filed: Aug. 31, 2018

(65) Prior Publication Data

US 2020/0073995 A1 Mar. 5, 2020

(51) Int. Cl.
*G06F 17/00* (2019.01)
*G06F 7/00* (2006.01)
(Continued)

(52) U.S. Cl.
CPC .......... *G06F 16/31* (2019.01); *G06F 16/334* (2019.01); *G06F 16/335* (2019.01); *G06F 16/93* (2019.01); *G16H 70/40* (2018.01)

(58) Field of Classification Search
CPC ........ G06F 16/31; G06F 16/334; G06F 16/93; G06F 16/335; G16H 70/40
(Continued)

(56) References Cited

U.S. PATENT DOCUMENTS 8,290,968 B2 * 10/2012 Jonas .................... G06F 16/285
707/756
2004/0220969 A1 11/2004 Cho et al.
(Continued)

FOREIGN PATENT DOCUMENTS

CN 110931084 A 3/2020

OTHER PUBLICATIONS

Tan et al. "Unified representation of genetic variants", Feb. 19, 2015, Oxford University Press, Bioinformatics 31(13), pp. 2202-2204 (Year: 2015).*

(Continued)

*Primary Examiner* — Pavan Mamillapalli
(74) *Attorney, Agent, or Firm* — Robert R. Aragona (57) ABSTRACT

A method, computer system, and a computer program product for automatically extracting and normalizing at least one mutant gene entity from at least one set of unstructured text is provided. The present invention may include extracting the unstructured text describing first and second entities. The present invention may then include identifying a specific first entity and a specific second entity. The present invention may also include associating the specific first and the specific second entities. The present invention may further include creating the mutant gene entity. The present invention may then include identifying at least one semantic relationship between the created mutant gene entity and one or more third entities. The present invention may further include storing the at least one set of data associated with the specific first and specific second entity, the semantic relationship, and the created mutant gene entity in a database.

25 Claims, 5 Drawing Sheets

(51) Int. Cl.
*G06F 16/31* (2019.01)
*G16H 70/40* (2018.01)
*G06F 16/93* (2019.01)
*G06F 16/33* (2019.01)
*G06F 16/335* (2019.01)

(58) Field of Classification Search
USPC .......................................................... 707/741
See application file for complete search history.

(56) References Cited

U.S. PATENT DOCUMENTS

| | | | |
|---|---|---|---|
| 2006/0053151 | A1 | 3/2006 | Gardner et al. |
| 2009/0019032 | A1* | 1/2009 | Bundschus ............ G16H 50/70 707/999.005 |
| 2014/0074864 | A1* | 3/2014 | Fontes ................ G06F 16/9535 707/748 |
| 2017/0046478 | A1* | 2/2017 | Agarwal ................ G16B 30/00 |

OTHER PUBLICATIONS

Ashique Mahmood et al., "DiMeX: A Text Mining System for Mutation-Disease Association Extraction," PLoS ONE, Apr. 13, 2016, p. 1-26, vol. 11, Issue 4.

Bundschus et al., "Extraction of Semantic Biomedical Relations from Text using Conditional Random Fields," BMC Bioinformatics, 2008, p. 1-14, vol. 9, Issue 207, BioMed Central Ltd.

Caporaso et al., "Mutationfinder: A High-Performance System for Extracting Point Mutation Mentions from Text," Bioinformatics, 2007, p. 1862-1865, vol. 23, Issue 14.

Chen et al., "IBM Watson: How Cognitive Computing Can Be Applied to Big Data Challenges in Life Sciences Research," Clinical Therapeutics, Apr. 2016, p. 688-701, vol. 38, No. 4.

Horn et al., "Automated Extraction of Mutation Data from the Literature: Application of MuteXt to G Protein-Coupled Receptors and Nuclear Hormone Receptors," Bioinformatics, 2004, p. 557-568, vol. 20, Issue 4, Oxford University Press.

Jimeno Yepes et al., "Towards Automatic Large-Scale Curation of Genomic Variation: Improving Coverage Based on Supplementary Material," Proceedings of BioLINK SIG, 2013, 5 Pages, Berlin, Germany.

Jimeno Yepes et al., "Literature Mining of Genetic Variants for Curation: Quantifying the Importance of Supplementary Material," Database, 2014, p. 1-12, vol. 2014, Article ID bau003, Oxford University Press.

Jimeno Yepes et al., "Mutation Extraction Tools can be Combined for Robust Recognition of Genetic Variants in the Literature," F1000Research, 2014, p. 1-27, vol. 3, Issue 18, Version 2.

Kim et al., "Overview of BioNLP'09 Shared Task on Event Extraction," Proceedings of the Workshop on BioNLP: Shared Task, Jun. 2009, p. 1-9, Association for Computational Linguistics, Boulder, Colorado.

Laurila et al., "Algorithms and Semantic Infrastructure for Mutation Impact Extraction and Grounding," BMC Genomics, 2010, p. 1-10, vol. 11, Supplement 4, BioMed Central Ltd.

Mell et al., "The NIST Definition of Cloud Computing," National Institute of Standards and Technology, Sep. 2011, p. 1-3, Special Publication 800-145.

Morgan et al., "Overview of BioCreative II Gene Normalization," Genome Biology, 2008, p. 1-19, vol. 9, Supplement 2, BioMed Central Ltd.

Percha et al., "Learning the Structure of Biomedical Relationships from Unstructured Text," PLoS Computational Biology, Jul. 28, 2015, p. 1-27, vol. 11, Issue 7.

Plazzer et al., "The InSiGHT Database: Utilizing 100 Years of Insights into Lynch Syndrome," Familial Cancer, 2013 p. 175-180, vol. 12, Issue 2, Springer Science+Business Media Dordrecht.

Ravikumar et al., "Text Mining Facilitates Database Curation—Extraction of Mutation-Disease Associations from Bio-Medical Literature," BMC Bioinformatics, 2015, p. 1-15, vol. 16, Issue 185.

Saqi et al., "Navigating the Disease Landscape: Knowledge Representations for Contextualizing Molecular Signatures," Briefings in Bioinformatics, 2018, p. 1-15, Oxford University Press.

Verspoor et al., "Annotating the Biomedical Literature for the Human Variome," Database, 2013, p. 1-13, vol. 2013, Article ID bat019, Oxford University Press.

* cited by examiner

EXTRACTION AND NORMALIZATION OF MUTANT GENES FROM UNSTRUCTURED TEXT FOR COGNITIVE SEARCH AND ANALYTICS

BACKGROUND

The present invention relates generally to the field of computing, and more particularly to genetics research and data processing.

Genes may be mutated in a plethora of ways, from a single nucleotide substitution to the deletion of an entire gene from a chromosome. Changes in the sequence of a gene have implications in the expression of genes into gene products (e.g., proteins). From a biological perspective, genetic mutations can underlie susceptibility to a disease, identify how a patient may react to a treatment due to a genetic predisposition, and identify new drug targets for the drug discovery pipeline. Mutated genes are considered one of the drivers of disease. Therefore, understanding from literature what and how genes are mutated and how these mutations give rise to biological consequences, such as disease susceptibility, is important for gaining an understanding of disease biology and possible treatment methods.

SUMMARY

Embodiments of the present invention disclose a method, computer system, and a computer program product for automatically extracting and normalizing at least one mutant gene entity from at least one set of unstructured text. The present invention may include extracting at least one set of unstructured text describing a first entity (e.g., a mutation entity) and a second entity (e.g., a gene entity). The present invention may then include identifying at least one specific first entity (e.g., at least one specific mutation entity) and at least one specific second entity (e.g., at least one specific gene entity) described in the extracted at least one set of unstructured text. The present invention may also include associating the identified at least one specific first entity with the corresponding identified at least one specific second entity. The present invention may further include creating the corresponding at least one mutant gene entity by consolidating at least one set of data associated with the associated at least one specific first entity with the corresponding associated at least one specific second entity. The present invention may then include identifying at least one semantic relationship between the created at least one mutant gene entity and one or more third entities. The present invention may further include storing the consolidated at least one set of data associated with the associated at least one specific first entity and the associated at least one specific second entity, the identified at least one semantic relationship, and the created at least one mutant gene entity in an annotation storage database.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for genetics research and data processing. As such, the present embodiment has the capacity to improve the technical fields of genetics research and data processing by performing an automatic extraction of at least one mention of at least one mutant gene from unstructured text utilizing a unified representation, and further semantically relate mutated genes to other concepts (e.g., drugs and diseases) by performing search and analytics on at least one representation associated with at least one mutated gene. More specifically, the automated mutant gene extraction program may retrieve at least one document from a corpus of documents stored in a document database. Then, the automated mutant gene extraction program may parse through the document(s) to identify and extract specific parts of the document(s) that describe a mutation or a gene. The automated mutant gene extraction program may then identify the particular mutation or particular gene described in the extracted text(s) of the document(s), and associate the identified mutation with a corresponding identified gene. The automated mutant gene extraction program may then consolidate the data associated with the specific gene and corresponding mutation to create one single mutant gene entity. The automated mutant gene extraction program may then identify at least one semantic relationship between the created mutant gene entity and other entities (e.g., drugs, disease) and store the information generated for the mutant gene entity, the supporting semantic relationship and the associated mutation and gene in an annotation storage database for search and analytics purposes.

As previously described, genes may be mutated in a plethora of ways, from a single nucleotide substitution to the deletion of an entire gene from a chromosome. Changes in the sequence of a gene have implications in the expression of genes into gene products (e.g., proteins). From a biological perspective, genetic mutations can underlie susceptibility to a disease, identify how a patient may react to a treatment due to a genetic predisposition, and identify new drug targets for the drug discovery pipeline. Mutated genes are considered one of the drivers of disease. Therefore, understanding from literature what and how genes are mutated and how these mutations give rise to biological consequences, such as disease susceptibility, is important for gaining an understanding of disease biology and possible treatment methods.

Since the majority of information related to genetic mutations is available in text format only (e.g., scientific literature), the information will be converted into a structured data format before any large-scale computational analysis can take place. Gene mutation databases are invaluable resources for researchers, enabling scientific advancements in many fields, e.g., drug discovery. Typically, these databases have been created by curating the scientific literature manually (e.g., InSight, also COSMIC and HGMD). However, generating a database can be a very time-consuming and error-prone process that cannot feasibly be applied to entire corpora of millions or more documents. Therefore, these databases can only represent a fraction of all available knowledge. As a result, an automated approach based on natural language processing is necessary, and while systems exist for the automated mining of gene information from free text, automatically extracting information that comprises an adequate understanding of the larger topic of gene mutations remains an unsolved problem.

Additionally, for mutation information to be valuable, the user should be able to understand the context of a mutation, for example the implications for other relevant concepts, such as diseases. As a first step, the process should identify mentions of mutation events in free text (e.g., deletions, substitutions, etc.) (i.e., creating mutation annotations). Since most important mutations take place within a gene, gene annotations may also be created, and subsequently, the mutation and gene annotations may be associated with one another to determine which gene is being mutated. However, such information may be complex and may be represented using a very wide range of different expressions in natural language. Moreover, correctly identifying relations between mutations and genes may only be an intermediate step, since the identified relations serve only to define the mutated gene and it may be additionally necessary to represent that mutated gene in a unified format to determine occurrences in other semantic relationships. Therefore, a unified representation of the mutated gene, disclosed and referred to as a mutant gene, may be necessary to enable cognitive search and analytics upon mutated genes for knowledge discovery.

For example, a key piece of knowledge may be that a particular mutated gene is associated with a particular disease. Accordingly, to represent this complex knowledge, several pieces of information (i.e., mutation, gene, relationship between each mutation and each gene represented as a mutant gene, disease, and the relationship between the mutant gene and the disease) must be extracted and understood (i.e., normalized) by the automated mutant gene extraction program for the purposes of cognitive search and analytics.

Therefore, it may be advantageous to, among other things, include, in the automated mutant gene extraction program, a substantial enhancement of existing natural language processing approaches, and further include multiple named entity recognition steps, multiple normalization steps and multiple nested layers of semantic relationship understanding to extract and normalize a mutant gene entity.

In the absence of the automated mutant gene extraction program, a user of a cognitive search and analytics system who is interested in documented evidence concerning mutated forms of genes must find manual or semi-manual ways to achieve the desired result, such as deliberately performing individual searches for specific genes, and then manually including text-based filters to focus the results (e.g., co-occurrence or proximity filters using specific phrases that describe particular mutations), a process that is not scalable and is prone to error and omission. Alternatively, and again in the absence of the automated mutant gene extraction program, some relevant information may be obtained by accessing manually curated databases of gene mentions (e.g., the InSiGHT database); however, since manually curated data cannot encompass the vast quantity of connections from across the entire literature space, such an approach may be limited to the fraction of the literature data that has been manually curated.

Furthermore, without the automatic mutation normalization component introduced herein, a user may have to manually search for multiple synonymous variants of the same concept in text (e.g., "T790M" and "Thr790Met" are synonymous). The automated mutant gene extraction program, therefore, addresses the needs of users whose interests concern understanding the breadth of information available about gene mutations, that, in the absence of the automated mutant gene extraction program which applies cognitive technology in this manner, is otherwise inaccessible to large-scale analysis.

According to at least one embodiment, the automated mutant gene extraction program may perform the automatic extraction of at least one mention of at least one mutant gene from unstructured text utilizing a unified representation. The automated mutant gene extraction program may further semantically relate mutated genes to other concepts (e.g., drugs and diseases) by performing search and analytics on at least one representation associated with at least one mutated gene. The present embodiment may include the extraction and then normalization of mentions of mutations and genes from free (e.g., unstructured) text (i.e., understanding that two distinct expressions of a mutation or gene can refer to the same mutation or gene), and the automatic association of a mutation and a gene in free text to be used in concert as an entity for analytics (i.e., as a mutant gene entity).

According to at least one embodiment, the automated mutant gene extraction program may include the automated extraction and normalization of mutations which occur in text, databases or other sources, comprising descriptions of mutation events of varying specificity (i.e., named entity recognition combined with named entity resolution, for mutations).

According to at least one embodiment, the automated mutant gene extraction program may include the automated extraction and normalization of genes which occur in text, databases or other sources, comprising descriptions of genes of varying specificity (i.e., named entity recognition combined with named entity resolution, for genes, which may include proteins, gene and protein fusions, etc.).

According to at least one embodiment, automated mutant gene extraction program may include the automated extraction of semantic associations between mutations and genes, occurring together in text (i.e., the identification of semantic relationships between these two concepts).

According to at least one embodiment, the automated mutant gene extraction program may include the automated storage and representation of the association between a mutation and a gene as an instance of a mutant gene entity. The mutant gene entity may then be considered as a special case of a gene entity. Representing the mutant gene as an entity, rather than just a semantic relationship between its constituent entities, may enable cognitive search and analytics utilizing mutant genes as entities (e.g., utilizing a knowledge graph, where the mutant gene is a graph node, a co-occurrence table, or other form of representation).

According to at least one embodiment, the automated mutant gene extraction program may enable the utilization of the mutant gene entity for previously infeasible discovery use cases (e.g., automatically generating a structured representation of how diseases are associated) with specific genes mutated in specific ways.

According to at least one embodiment, the automated mutant gene extraction program may include a cognitive search and analytics component that may support discovery use cases concerning mutant genes in addition to and without compromising the ability of the automated mutant gene extraction program to support discovery use cases concerning unaltered genes.

According to at least one embodiment, the concept of performing cognitive search and analytics on a mutant gene entity by the automated mutant gene extraction program may be more than an incremental improvement on existing cognitive search and analytics capabilities utilizing entities relevant to the life sciences (e.g., genes, drugs and diseases). While entities usually occur in unstructured text as individual noun phrases, a mutant gene may typically be defined by multiple noun phrases or other pieces of text that may identify the mutation event, and the gene being mutated. Thus, the automated mutant gene extraction program may subsequently normalize which specific mutation and which specific gene are being discussed, and may associate them to one another through identification of a semantic relationship. Through the association of the semantic relationship, additional layers of nested semantic relationship understanding may be achieved by treating the mutant gene itself as an entity, which may be the agent or the target of a semantic relationship. Accordingly, the automated mutant gene extraction program may include more than an incremental increase in complexity compared to existing methods.

According to at least one embodiment, the automated mutant gene extraction program may include the uploading of a corpus of documents (i.e., unstructured text documents). The unstructured text documents may be analyzed and stored in a database for access by subsequent components of the automated mutant gene extraction program.

According to at least one embodiment, the automated mutant gene extraction program may include Gene Annotation and Mutation Annotation components. The Gene Annotation and Mutation Annotation components may perform named entity recognition for genes and mutations, respectively (i.e., identifying the specific parts of text that describe genes and mutations). In the present embodiment, other components (e.g., Disease Annotation and Drug Annotation components) may also exist in the automated mutant gene extraction program.

According to at least one embodiment, the automated mutant gene extraction program may include Gene Normalization and Mutation Normalization components. The Gene Normalization and Mutation Normalization components may perform named entity resolution (normalization) for genes and mutations respectively (i.e., identifying which particular gene or mutation is being described by the text identified in the preceding components). As an example, gene annotations "EGFR" and "epidermal growth factor receptor" would be considered as synonymous, and when normalized would be represented as the same concept (e.g., EGFR, the normalized form used herein). Similarly, for example, mutation annotations "T790M" and "Thr790Met" may be considered as synonymous, and when normalized may be represented as the same concept (e.g., P.T790M, the normalized form used herein). In the present embodiment, other components (e.g., Disease Normalization and Drug Normalization components) may also exist in the automated mutant gene extraction program.

According to at least one embodiment, the automated mutant gene extraction program may include a Mutant Gene Annotation component which performs the semantic relationship association of genes and mutations. Through natural language processing applied to specific sentences or other sections of text that contain both a gene and a mutation annotation, each mutation can be associated with the gene that the mutation is occurring on. For example, the mutation annotation "T790M" would be associated with the gene annotation "epidermal growth factor receptor" through the phrase "variant of". Accordingly, a mutant gene annotation may be created, comprising the association between these specific mutation and gene annotations. In general, through semantic processing of natural language, the Mutant Gene Annotation component may identify such associations in the various arrangements that they may occur in free text. Genes and mutations that may not be successfully associated with one another are unable to create mutant genes.

According to at least one embodiment, the automated mutant gene extraction program may include a Mutant Gene Normalization component that normalizes each mutant gene by combining the normalized forms of the mutation and the gene. For example, if the normalized form of "T790M" is "P.T790M", and the normalized form of "epidermal growth factor receptor" is "EGFR", then the normalized form of the mutant gene would be some combination of these elements, such as "EGFR//P.T790M".

According to at least one embodiment, the automated mutant gene extraction program may include a Semantic Relationship Annotation component that performs the second layer of semantic relationship annotation, comprising the association of all computed annotations, including the mutant genes. Through natural language processing applied to specific sentences or other sections of text that contain more than one annotation, specific semantic relationships of importance may be identified, including between mutant genes and other entities (e.g., drugs and diseases). For example, the mutant gene identified and normalized as "EGFR//P.T790M" would be associated with the drug "Erlotinib" through the phrase "resistance of" (or "evaluation of the resistance of") which precedes the mutant gene, and "to" (or "to cancer drug") which follows. In general, through semantic processing of natural language, the Semantic Relationship Annotation component may identify such associations in the various arrangements that they may occur in free text.

According to at least one embodiment, the automated mutant gene extraction program may include an Annotation Storage component that collects, indexes and otherwise stores the computed annotations for downstream cognitive search and analytics purposes.

Figure 1:
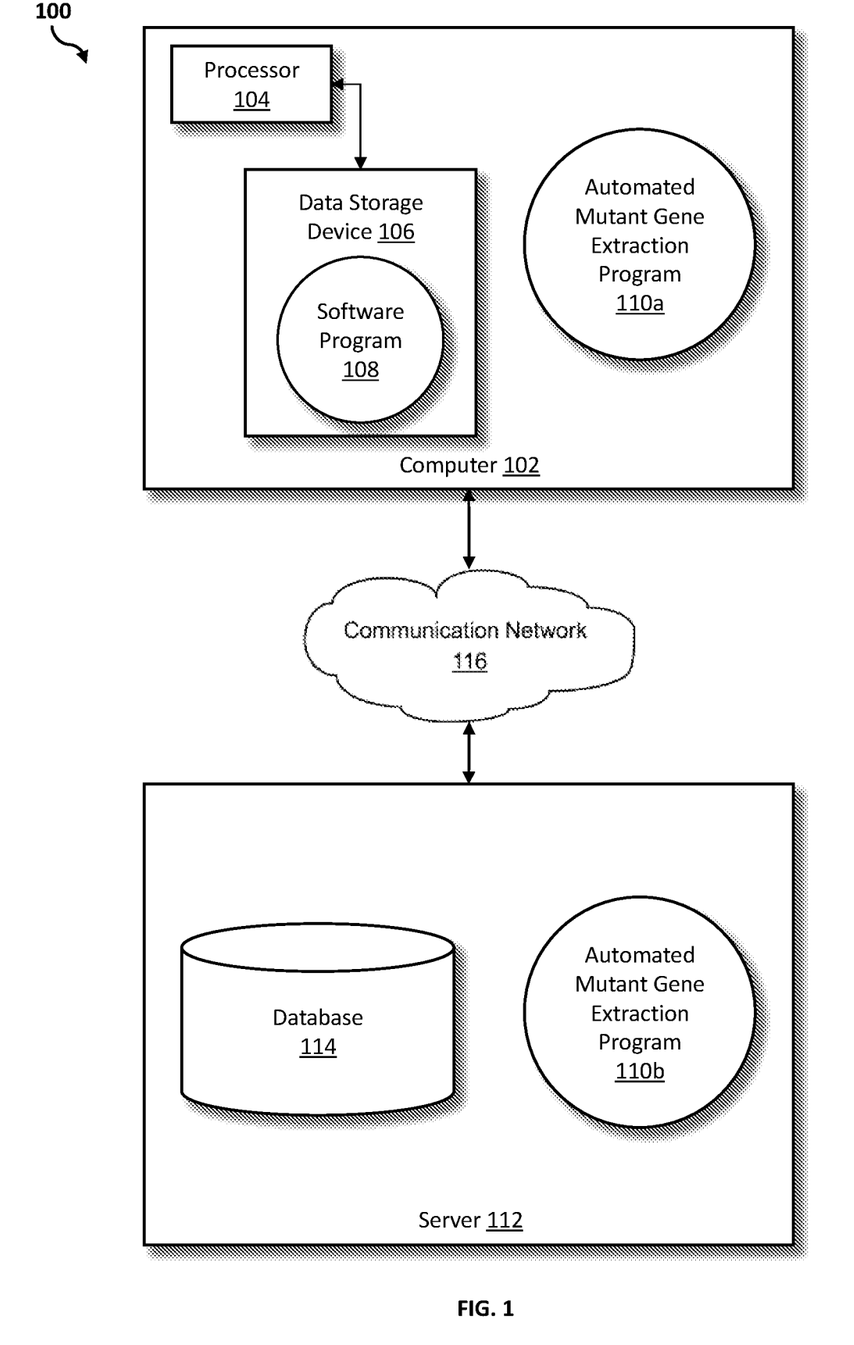
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an automated mutant gene extraction program 110a. The networked computer environment 100 may also include a server 112 that is enabled to run an automated mutant gene extraction program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the automated mutant gene extraction program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the automated mutant gene extraction program 110a, 110b (respectively) to automate mutant gene extraction. The automated mutant gene extraction method is explained in more detail below with respect to FIG. 2.

Figure 2:
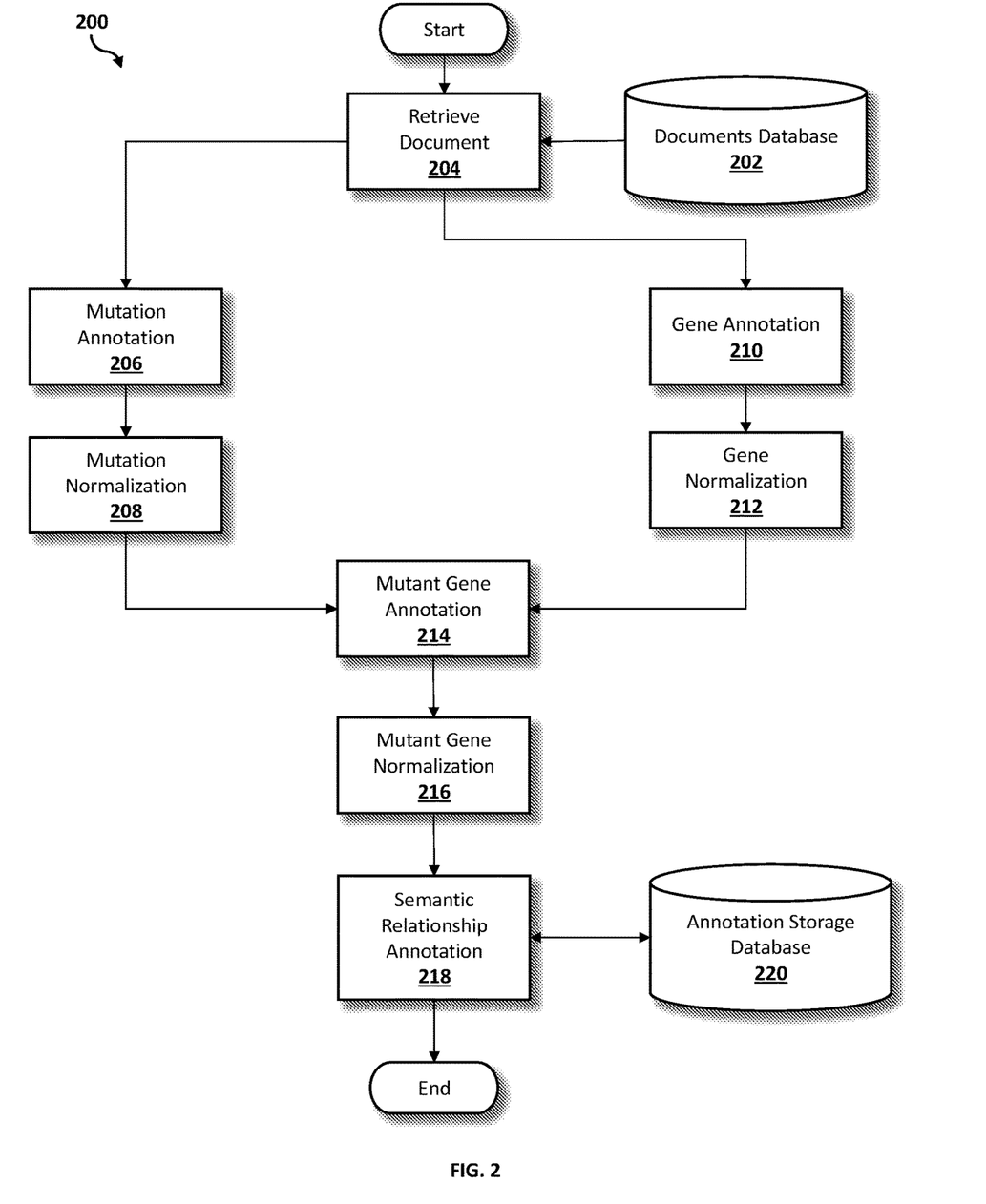
FIG. 2 is an operational flowchart illustrating a process for automatically extracting and normalizing at least one mutant gene according to at least one embodiment.

Referring now to FIG. 2, an operational flowchart illustrating the exemplary automated mutant gene extraction and normalization process 200 used by the automated mutant gene extraction program 110a, 110b according to at least one embodiment is depicted.

At 204, at least one document is retrieved from a documents database 202 (i.e., database 114). Using a software program 108 on the user device (e.g., user's computer 102), the automated mutant gene extraction program 110a, 110b may retrieve (i.e., pull or upload) at least one document as input from the documents database 202 on the server 112 or a cloud storage service via communications network 116. The documents (e.g., medical or scientific abstracts, full text scientific articles, full text patents, clinical trial reports, drug labels, medical or scientific literature, and secondary internet sources) may include unstructured text or free text. A corpus of documents may be stored in the documents database 202. Alternatively, the user may manually upload document(s), without the use of the server 112 or a cloud storage service.

For example, the automated mutant gene extraction program 110a, 110b selects a new article in a prestigious science journal, "Genetics World," published in Summer 2017 in regard to new genetics research on the BRAF gene, which is a human gene that encodes a protein called B-Raf that is involved in sending signals inside cells that are directly involved in cellular growth, from the documents database 202. The article was recently uploaded into the documents database 202, and has yet to be annotated by the automated mutant gene extraction program 110a, 110b.

In another embodiment, the automated mutant gene extraction program 110a, 110b may be automatically updated, on a periodic basis (e.g., every few weeks) with the latest or amended publications based on a set of parameters (e.g., specific type of genes, drugs, diseases, mutations, or area of genomic research) set by the user or an administrator.

In another embodiment, the automated mutant gene extraction program 110a, 110b may include an alert associated with particular group of scientific literature (e.g., type of journal, publication or internet source) or parameters (e.g., specific type of genes, drugs, diseases, mutations, or area of genomic research) in which the automated mutant gene extraction program 110a, 110b may receive an alert or notification on any updates on any document or set of parameters included in the corpus of documents within the documents database 202. The user or an administrator may also be notified of such an update. The automated mutant gene extraction program 110a, 110b may then proceed with updating the document accordingly.

In another embodiment, the user or an administrator may manually accept or reject the amended or latest document after receiving a notification or alert associated with the updated or amended document. If the user or administrator rejects the amended or latest document, then the automated mutant gene extraction program 110a, 110b may include, as metadata, a notification with the associated document(s) in the documents database 202 notifying of the updated or amended documents and information (e.g., publication date of updated or amended document, date of rejection, name of person who implemented the rejection, a reason for the rejection, link to the updated or amended document). In at least one embodiment, the same metadata (i.e., including notification of the updated or amended document(s) and corresponding information) may be included with any other databases associated with the automated mutant gene extraction program 110a, 110b.

The automated mutant gene extraction program 110a, 110b may build the document database 202 by utilizing a software program 108 on the user device (e.g., user's computer 102) to upload the corpus of documents from the server 112, internet, or a cloud storage service via communications network 116. Alternatively, documents may be manually uploaded by the user and stored in the documents database 202. The documents within the documents database 202 may be indexed based on the type of document, the subject matter included within the document, or other user preferences, which may be configured by the user or administrator of the automated mutant gene extraction program 110a, 110b. Unless specified by user preferences, the automated mutant gene extraction program 110a, 110b may include minimal, if any, limitations on the number of documents that may be included in the documents database 202.

Next, at 206, the mutation annotation is commenced. In the mutation annotation component, the automated mutant gene extraction program 110a, 110b may utilize a software program 108 (e.g., an application of one or more natural language processing techniques) on the user device (e.g., user's computer 102) for the identification and extraction of one or more specific parts of the one or more unstructured text(s) (i.e., source text or source data) in the one or more retrieved document(s) (i.e., source document(s)) that describe one or more mutations (i.e., mutation entity or mutation entities). The automated mutant gene extraction program 110a, 110b may utilize a known engine to parse through the unstructured text for mutations. The output of the mutation annotation component (i.e., mutation annotation phase) may constitute a form of data representation including records of mutations in the source data (e.g., information about the retrieved document(s) (i.e., one or more documents in which the at least one set of data was derived from), the location in the text, the word or phrase representing the mutation in question, and surrounding context). In the context of a natural language processing-based embodiment, the mutation annotation component may be considered as the named entity recognition phase.

Continuing the previous example, the automated mutant gene extraction program 110a, 110b utilized a software tool to parse through the article, and the software tool identified one section of text within the article states:

"A distinct mutation in BRAF (codon K600E) was detected in three cases of follicular variant of papillary thyroid carcinoma (PTC)."

The automated mutant gene extraction program 110a, 110b identified that the text describes a mutation, and therefore, the automated mutant gene extraction program 110a, 110b extracted that text from the article. Along with the identified and extracted text, the automated mutant gene extraction program 110a, 110b includes that the text was located on page 57, lines 21-22 of the article in the prestigious "Genetics World" science journal published in Summer 2017, as well as screenshots of the surrounding four sentences before and after the extracted text for context to the extracted text.

In another embodiment, the automated mutant gene extraction program 110a, 110b may identify and extract text that provide limited information on the mutation. For example, the automated mutant gene extraction program 110a, 110b may identify and extract the following text: "BRAF mutations are associated with some histological types of papillary thyroid carcinoma." As such, the way that the gene is mutated is not specifically described; however, there is a clear inference that some type of BRAF mutation occurred and that the BRAF mutation(s) is related to a disease, papillary thyroid carcinoma.

In another embodiment, the automated mutant gene extraction program 110a, 110b may identify and extract text that does not provide a name for the mutation and instead provides a specific type of conversion caused by the mutation. For example, the automated mutant gene extraction program 110a, 110b may identify and extract the following text: "The G:C to A:T transitions (11 of 28: 39%) were the most frequent p53 mutations found and clustered in tumors from lifetime nonsmokers without passive smoke exposure." As such, the mutation is a specific type of conversion in the sequence of p53.

In another embodiment, the automated mutant gene extraction program 110a, 110b may include a disease annotation component (i.e., disease annotation phase) for the identification and extraction of text in the retrieved document that describes a particular disease.

Then, at 208, the mutation normalization is commenced. The automated mutant gene extraction program 110a, 110b may include a mutation normalization component (i.e., mutation normalization phase), utilizing a software program 108 on the user device (e.g., user's computer 102) for identifying which one or more mutations are described by the unstructured text of the retrieved source document in the mutation annotation component 206. The automated mutant gene extraction program 110a, 110b may also utilize a variety of techniques (e.g., to cross-reference other data sources based on expert curated data, application of software tools, leverage (or not leverage) document context, document metadata, annotations generated from diseases or drugs) implemented by an engine or software application to identify one or more mutations in the unstructured text of the retrieved source document.

Continuing the previous example, the automated mutant gene extraction program 110a, 110b cross-referenced other data sources based on expert curated data integrated with the automated mutant gene extraction program 110a, 110b to identify that the specific mutation included in the text was codon K600E.

In another embodiment, the automated mutant gene extraction program 110a, 110b may include a disease normalization component (i.e., disease normalization phase) for identifying a particular disease.

Then, at 210, the gene annotation is commenced. Similar to the mutation annotation component 206, in the gene annotation component, the automated mutant gene extraction program 110a, 110b may utilize a software program 108 (e.g., an application of one or more natural language processing techniques) on the user device (e.g., user's computer 102) for the identification and extraction of one or more specific parts of the one or more unstructured text(s) (i.e., source text or source data) in the one or more retrieved document(s) (i.e., source document(s)) that describe one or more genes (i.e., gene entity or gene entities). The automated mutant gene extraction program 110a, 110b may utilize a known engine to parse through the unstructured text for genes. The output of the gene annotation component (i.e., gene annotation phase) may constitute a form of data representation including records of genes in the source data (e.g., information about the retrieved document(s) (i.e., one or more documents in which the at least one set of data was derived from), the location in the text, the word or phrase representing the gene in question, and surrounding context). In the context of a natural language processing-based embodiment, the gene annotation component may be considered as the named entity recognition phase.

Continuing the previous example, separate and independent of mutation annotation 206 and mutation normalization 208, the automated mutant gene extraction program 110a, 110b parsed through the same article of the prestigious "Genetics World" science journal, and identified and extracted the same text:

"A distinct mutation in BRAF (codon K600E) was detected in three cases of follicular variant of papillary thyroid carcinoma (PTC)."

In the present embodiment, the automated mutant gene extraction program 110a, 110b may treat the mutation annotation 206 and the gene annotation 210 as independent and separate processes in which the downstream components rely on the results of each mutation annotation 206 and gene annotation 210 to identify, extract and normalize the mutant gene. As such, the automated mutant gene extraction program 110a, 110b may run the mutation annotation 206 and the gene annotation 210 in serial either consecutively or simultaneously to each other. For example, in a multi-threaded implementation in which each processing thread has a separate document pool associated with the documents database 202, iteratively, the automated mutant gene extraction program 110a, 110b may grab or retrieve the next document, and execute each of the components on that document in serial, as a part of a larger parallel processing approach.

In the present embodiment, the automated mutant gene extraction program 110a, 110b may perform the mutation annotation 206 and the gene annotation 210 consecutively. For example, the automated mutant gene extraction program 110a, 110b may perform the mutation annotation 206 before the gene annotation 210, or the automated mutant gene extraction program 110a, 110b may perform the gene annotation 210 before the mutation annotation 206.

In another embodiment, the automated mutant gene extraction program 110a, 110b may perform the mutation annotation 206 and the gene annotation 210 simultaneously. For example, the automated mutant gene extraction program 110a, 110b may separately perform the mutation annotation 206 and the gene annotation 210 at the same time.

In another embodiment, the automated mutant gene extraction program 110a, 110b may include a drug annotation component (i.e., drug annotation phase) for the identification and extraction of text in the retrieved document that describes a particular drug.

In another embodiment, the automated mutant gene extraction program 110a, 110b may utilize any manner of natural language processing (NLP) technology on either the mutation annotation 206 and the gene annotation 210. Since the mutation annotation 206 and the gene annotation 210 are independent and separate processes, the automated mutant gene extraction program 110a, 110b may utilize different NLP technology for each component. For example, the mutation annotation 206 may be rules-based supported by an expert-curated dictionary, while the gene annotation 210 is performed using a machine learning model trained on expert-curated examples. The automated mutant gene extraction program 110a, 110b may include minimal, if any, restrictions on the type of NLP technology that may be utilized by the mutation annotation 206 and the gene annotation 210.

Then, at 212, the gene normalization is commenced. The automated mutant gene extraction program 110a, 110b may include a gene normalization component (i.e., gene normalization phase), utilizing a software program 108 on the user device (e.g., user's computer 102) for identifying which one or more genes are described by the unstructured text of the retrieved source document in the gene annotation component 210. The automated mutant gene extraction program 110a, 110b may also utilize a variety of techniques (e.g., to cross-reference other data sources based on expert curated data, application of software tools, leverage (or not leverage) document context, document metadata, annotations generated from diseases or drugs) implemented by an engine or software application to identify one or more genes in the unstructured text of the retrieved source document.

Continuing the previous example, the automated mutant gene extraction program 110a, 110b utilizes an application of software tools that identifies gene mentions based on a list of previously discovered genes to identify the specific gene included in the text. The application matched the BRAF gene mentioned in the extracted text with the BRAF gene listed on the application.

In the present embodiment, similar to the mutation annotation 206 and the gene annotation 210, the automated mutant gene extraction program 110a, 110b may treat the mutation normalization 208 and the gene normalization 212 as independent and separate processes in which the downstream components rely on the results of each the mutation normalization 208 and the gene normalization 212 to normalize the mutant gene. As such, the automated mutant gene extraction program 110a, 110b may run the mutation normalization 208 and the gene normalization 212 in serial either consecutively or simultaneously to each other.

In the present embodiment, similar to the mutation annotation 206 and the gene annotation 210, the automated mutant gene extraction program 110a, 110b may perform the mutation normalization 208 and the gene normalization 212 consecutively. For example, the automated mutant gene extraction program 110a, 110b may perform the mutation normalization 208 before the gene normalization 212, or the automated mutant gene extraction program 110a, 110b may perform the gene normalization 212 before the mutation normalization 208.

In another embodiment, the automated mutant gene extraction program 110a, 110b may perform the mutation normalization 208 and the gene normalization 212 simultaneously. For example, the automated mutant gene extraction program 110a, 110b may separately perform the mutation normalization 208 and the gene normalization 212 at the same time.

In another embodiment, similar to mutation annotation 206 and gene annotation 210, the automated mutant gene extraction program 110a, 110b may utilize any manner of technology (e.g., dictionary look-up for synonyms, semantic context modeling) on either the mutation normalization 208 and the gene normalization 212. Since the mutation normalization 208 and the gene normalization 212 are independent and separate processes, the automated mutant gene extraction program 110a, 110b may utilize different types of technology for each component. For example, the mutation normalization 208 may utilize dictionary look-ups for synonyms or related words or phrases, while the gene normalization 212 may utilize a semantic context modeling approach. The automated mutant gene extraction program 110a, 110b may include minimal, if any, restrictions on the type of NLP technology that may be utilized by the mutation normalization 208 and the gene normalization 212.

In another embodiment, the automated mutant gene extraction program 110a, 110b may include a drug normalization component (i.e., drug normalization phase) for identifying a particular drug.

Then, at 214, the mutant gene annotation is commenced. The automated mutant gene extraction program 110a, 110b may include a mutant gene annotation component (i.e., mutant gene annotation phase), performing a first layer of semantic relationship association of one or more genes and one or more mutations. The automated mutant gene extraction program 110a, 110b may associate (i.e., link) one or more genes with one or more mutations annotated and normalized in the preceding components, namely for one or more mutations, processed at mutation annotation 206 and mutation normalization 208, and for one or more genes, processed at gene annotation 210 and gene normalization 212. Through natural language processing (NLP) techniques applied to specific sentences or other sections of the unstructured text of the retrieved source document that included both a gene annotation and a mutation annotation, the automated mutant gene extraction program 110a, 110b may associate each mutation with one or more genes, whose deoxyribonucleic acid (DNA) sequence was altered by the mutation.

Each mutant gene annotation created by the automated mutant gene extraction program 110a, 110b may include the association between a specific mutation annotation and a specific gene annotation. Through the NLP processing of semantic relationships, the automated mutant gene extraction program 110a, 110b may identify these semantic relationship associations in various arrangements (e.g., association between a specific disease and a specific drug) that may occur in unstructured text in at least one retrieved source document.

The automated mutant gene extraction program 110a, 110b may utilize the first layer of semantic relationship association of one or more genes and one or more mutations during mutant gene annotation 214 to confirm whether a gene and a mutation discovered in the retrieved document(s) are not merely occurring in the same sentence or document. Instead, the gene and mutation discovered in the retrieved document(s) may be related in such a way as to convey that the particular gene is being mutated in a particular way. The result of mutant gene annotation 214 may include annotations of mutated genes (i.e., a type of annotation that includes a mutation and a gene that are related).

Continuing the previous example, the automated mutant gene extraction program 110a, 110b reviewed the data annotated and normalized from the preceding components (i.e., mutation annotation 206, mutation normalization 208, gene annotation 210 and gene normalization 212) to associate the identified mutation, codon K600E, in the extracted text with the corresponding identified gene, BRAF gene, also from the extracted text.

In the present embodiment, the automated mutant gene extraction program 110a, 110b may present an error message if a specific mutation may not be associated with a specific gene, or a specific gene may not be associated with a specific mutation by the automated mutant gene extraction program 110a, 110b. Additionally, the automated mutant gene extraction program 110a, 110b may fail to create a mutant gene (i.e., combination of the specific mutation and the specific gene) for such an unsuccessful association between a specific gene and a specific mutation.

Then, at 216, the mutant gene normalization is commenced. The automated mutant gene extraction program 110a, 110b may include a mutant gene normalization component (i.e., mutant gene normalization phase), which may normalize each mutant gene created in the mutant gene annotation component 214 by combining the normalized form of the mutation from the preceding mutation normalization component 208 and the normalized form of the gene from the preceding gene normalization component 212. The mutant gene normalization component 216 may restructure the data associated with a specific mutation and a specific gene that created a specific mutant gene into one single mutant gene entity to reduce redundancy and to improve data integrity.

Continuing the previous example, the automated mutant gene extraction program 110a, 110b consolidates all the data generated in the preceding components (i.e., mutation annotation 206, mutation normalization 208, gene annotation 210 and gene normalization 212) for codon K600E and BRAF gene into one mutant gene entity, BRAF//P.K600E. The data includes the location of the extracted text, (page 57, lines 21-22 of the article in the "Genetics World" science journal published in Summer 2017), the name of mutation (codon K600E), name of the gene (BRAF gene), and screenshots of the surrounding four sentences before and after the extracted text for context to the extracted text.

Then, at 218, the semantic relationship annotation is commenced. The automated mutant gene extraction program 110a, 110b may include a semantic relationship annotation component, performing a second layer of semantic relationship annotation for the association of any computed annotations, including mutant genes. Similar to the first layer of semantic relationship association during mutant gene annotation 214, the automated mutant gene extraction program 110a, 110b may utilize NLP techniques applied to specific sentences or other sections (e.g., paragraphs, diagram descriptions) of the unstructured text of a retrieved source document that includes more than one annotation. The automated mutant gene extraction program 110a, 110b may identify the specific semantic relationships of importance (e.g., relevant mutant gene to a particular disease) between the mutant genes and other entities (e.g., diseases and drugs). For example, if having Mutant Gene XYZ exponentially increases a person's risk of developing lung cancer, then any mention of either Mutant Gene XYZ and lung cancer, or the relationship between Mutant Gene XYZ and lung cancer in the document text may be considered as being a relevant relationship (i.e., semantic relationship of importance). As such, the mutations, genes, diseases, drugs and other entities (i.e., organism, condition, or substance) that may be relevant or a part of an identified specific semantic relationship of importance depending on the user, administrator, type of research conducted, or other factors (e.g., recent discovery, area of interest or focus for the user or administrator, grant restrictions or grant details) may be identified and annotated.

The output of the semantic relationship annotation component 218 (i.e., the computed annotations) may be stored in the annotation storage database 220 (i.e., database 114) for downstream cognitive search and analytics purposes. The annotation storage database 220 may include the extracted and normalized mutant genes, the corresponding mutation(s) and gene(s), retrieved document text associated with the mutant genes and the corresponding mutation(s) and gene (s), and other identifiers (e.g., document metadata, document identifications and related features).

Additionally, the created mutant gene entity (i.e., mutant gene) may become a searchable object in the annotation storage database 220. Therefore, the user may search via the mutant gene to research the consequences of having a particular gene mutated in a particular way, or discover downstream effects (e.g., diseases and possible treatments) associated with the particular mutated gene.

In at least one embodiment, the second layer of semantic relationship annotation 218 may be considered the downstream component of the first semantic relationship annotation during the mutant gene annotation 214. The semantic relationship annotation 218 may analyze the extracted and normalized mutant genes from 216 with the semantic relationships generated in the mutation gene annotation 214. For example, analyzing the Mutant Gene XYZ to determine that the presence of Mutant Gene XYZ increases the risk of other respiratory related conditions, such as lung cancer, bronchitis and mesothelioma.

Continuing the previous example, the automated mutant gene extraction program 110a, 110b analyzed the extracted and normalized mutant gene BRAF//P.K600E and the identified and extracted text to identify a semantic relationship between the mutant gene BRAF//P.K600E and any other entity in the extracted text or surrounding text associated with the extracted text. The automated mutant gene extraction program 110a, 110b identified that there is a relationship between mutant gene BRAF//P.K600E and the disease, PTC, specifically in the follicular variant of PTC. This relationship, with mutant gene BRAF//P.K600E and PTC, as well as any supporting information, such as the location of the extracted text, (page 57, lines 21-22 of the article in the "Genetics World" science journal published in Summer 2017), the name of mutation (codon K600E), name of the gene (BRAF gene), and screenshots of the surrounding four sentences before and after the extracted text for context to the extracted text, are saved as metadata in the document in the annotation storage database 220. Additionally, the mutant gene, BRAF//P.K600E, becomes a searchable object in the annotation storage database 220 for search and analytics purposes.

In the present embodiment, the automated mutant gene extraction program 110a, 110b may extract and normalize mentions of the mutations and genes (separately and independently) from free text or unstructured text within a document, and automatically associate a mutation and a gene in free text to be used on concert as an entity for analytics (i.e., mutant gene entity).

In another embodiment, the documents database 202 may be separate from the annotation storage database 220, which includes the features that denote the document identifications (i.e., document IDs) and positions within the documents at which the features occur. In another embodiment, the document database 202 and the annotation storage database 220 are the same database in which the annotations may be stored in the documents (e.g., metadata), and may be updated accordingly.

In one embodiment, the document database 202 and the annotation storage database 220 may be a global database in which user access may be restricted. As such, the documents and annotations associated with the mutant gene extracted and normalized by the automated mutant gene extraction program 110a, 110b for any user may be included in the document database 202 and the annotation storage database 220. For example, if a user provides private and confidential information regarding Mutant Gene ABC that a specific research group associated with the user is testing, then the data associated with the annotations of Mutant Gene ABC may be stored with corresponding privilege information such that only users from that specific research group may access that data.

In another embodiment, the document database 202 and the annotation storage database 220 may include at least one local database on a user's device (e.g., user's computer 102), with all data storage and processing occurring locally to that user. The data may be limited to an individual user or specific group associated with a user. For example, one research facility or group may have one local database. The local database(s) may store and index the documents and features associated with the annotations in each of or both document database 202 and the annotation storage database 220, which may include each annotation and corresponding document(s) within all the local databases.

In another embodiment, the document database 202 and the annotation storage database 220 may include at least one local database on a user's device (e.g., user's computer 102), in addition to at least one global database associated with both or each document database 202 and annotation storage database 220. The local database(s) may periodically store and index the documents and features associated with the annotations in the global database(s) associated with each of or both document database 202 and the annotation storage database 220, which may include each annotation and corresponding document(s) within all the local databases. The user may, through limited user access, retrieve documents and annotations not stored and indexed on the local database, but rather only stored and indexed on at least one global database.

In another embodiment, the automated mutant gene extraction program 110a, 110b may utilize a solr (i.e., open source enterprise search platform) index to store annotations, where the document IDs are features of the annotations, in the annotation storage database 220. The user may then be able to identify documents with a particular annotation by querying the solr index for that annotation, and retrieving the corresponding document IDs from the annotation storage index 220. For example, mutant gene annotations, as well as gene and mutation annotations may be indexed by solr index to facilitate search and analytics on those annotations. In the present embodiment, within Watson for Drug Discovery™ (WDD) (e.g., Watson for Drug Discovery™, Watson for Drug Discovery and all Watson for Drug Discovery-based trademarks and logos are trademarks or registered trademarks of International Business Machines Corporation and/or its affiliates), genes, mutations, and mutant genes may be indexed in a similar matter, within the annotation storage database 220, to support search and analytics on any annotation type.

In the present embodiment, the automated mutant gene extraction program 110a, 110b may be run in an automated manner without intervention (i.e., human intervention) occurring during the automated mutant gene extraction and normalization program process 200 (i.e., pipeline). However, in at least one other embodiment, human feedback (i.e., feedback or user feedback) may be supported, through a front end, where annotation errors or omissions are reported using a graphical user interface (GUI), and the received feedback may be directed to the updating or improvement of machine learning models, dictionaries or the related technology or application tools associated with the annotation error or omission between each execution of the pipeline. Alternatively, in another embodiment, perhaps for a smaller scale implementation, the user may pause and interrupt the pipeline to change or implement modifications at any component or phase of the pipeline.

In another embodiment, the automated mutant gene extraction program 110a, 110b may periodically update new or amended documents in the documents database 202, and the pipeline may periodically re-run, which may include periodic updates to the other components and save the updates to the documents database 202 and the annotation storage database 220. The updates may further be utilized to re-train machine learning models based on the latest training data and/or updated documents.

In the absence of the automated mutant gene extraction program 110a, 110b, the user of a cognitive search and analytics system who is interested in documented evidence concerning mutated forms of genes may have to find manual or semi-manual ways to achieve the desired result, such as deliberately performing individual searches for specific genes, and then manually including text-based filters to focus the results (e.g., co-occurrence or proximity filters using specific phrases that describe particular mutations), a process that may not be scalable and may be prone to error and omission. Alternatively, and again in the absence of the automated mutant gene extraction program 110a, 110b, some relevant information may be obtained by accessing manually curated databases of gene mentions. However, manually curated data that are retrieved may be limited to a fraction of the literature data.

Therefore, the functionality of a computer may be improved by the automated mutant gene extraction program 110a, 110b because the automated mutant gene extraction program 110a, 110b may be utilized to configure a cognitive system, such as WDD™, to understand and convey information to the user about gene mutations, through the concept of a "mutant gene entity" (i.e., a complex new entity type which requires a combination of multiple natural language processing methods to achieve). The automated mutant gene extraction program 110a, 110b represents more than an incremental improvement on the existing capabilities and functionalities of the computer.

It may be appreciated that FIG. 2 provides only an illustration of one embodiment and does not imply any limitations with regard to how different embodiments may be implemented. Many modifications to the depicted embodiment(s) may be made based on design and implementation requirements.

Figure 3:
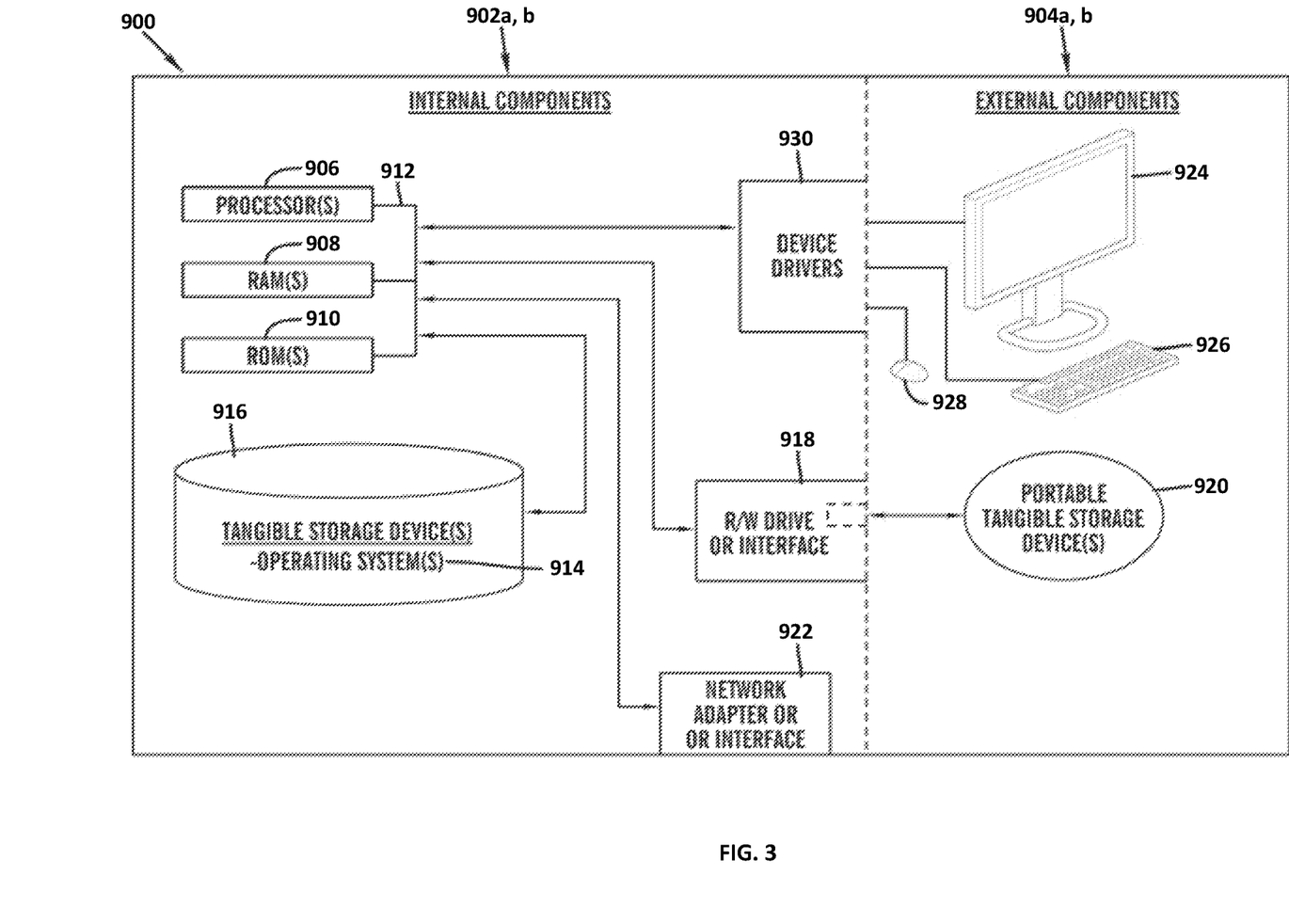
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the automated mutant gene extraction program 110a in client computer 102, and the automated mutant gene extraction program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the automated mutant gene extraction program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the automated mutant gene extraction program 110a in client computer 102 and the automated mutant gene extraction program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the automated mutant gene extraction program 110a in client computer 102 and the automated mutant gene extraction program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
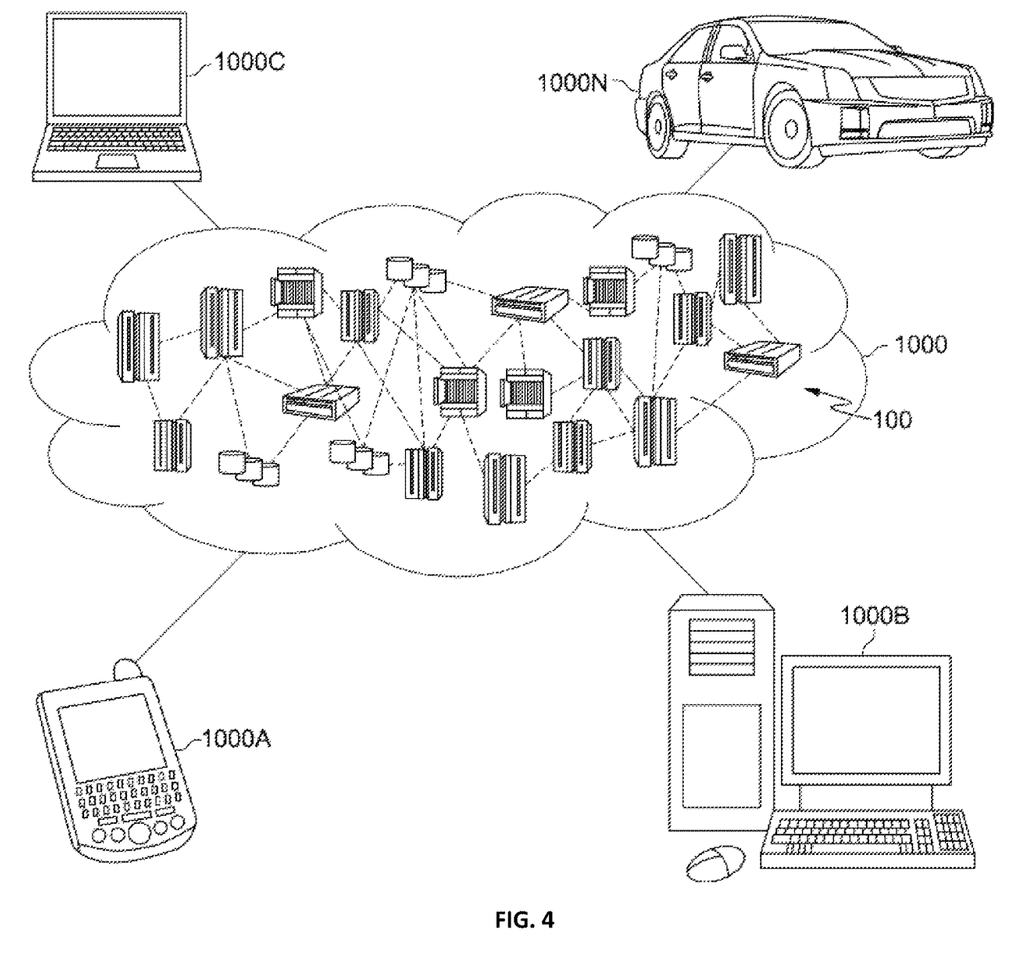
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
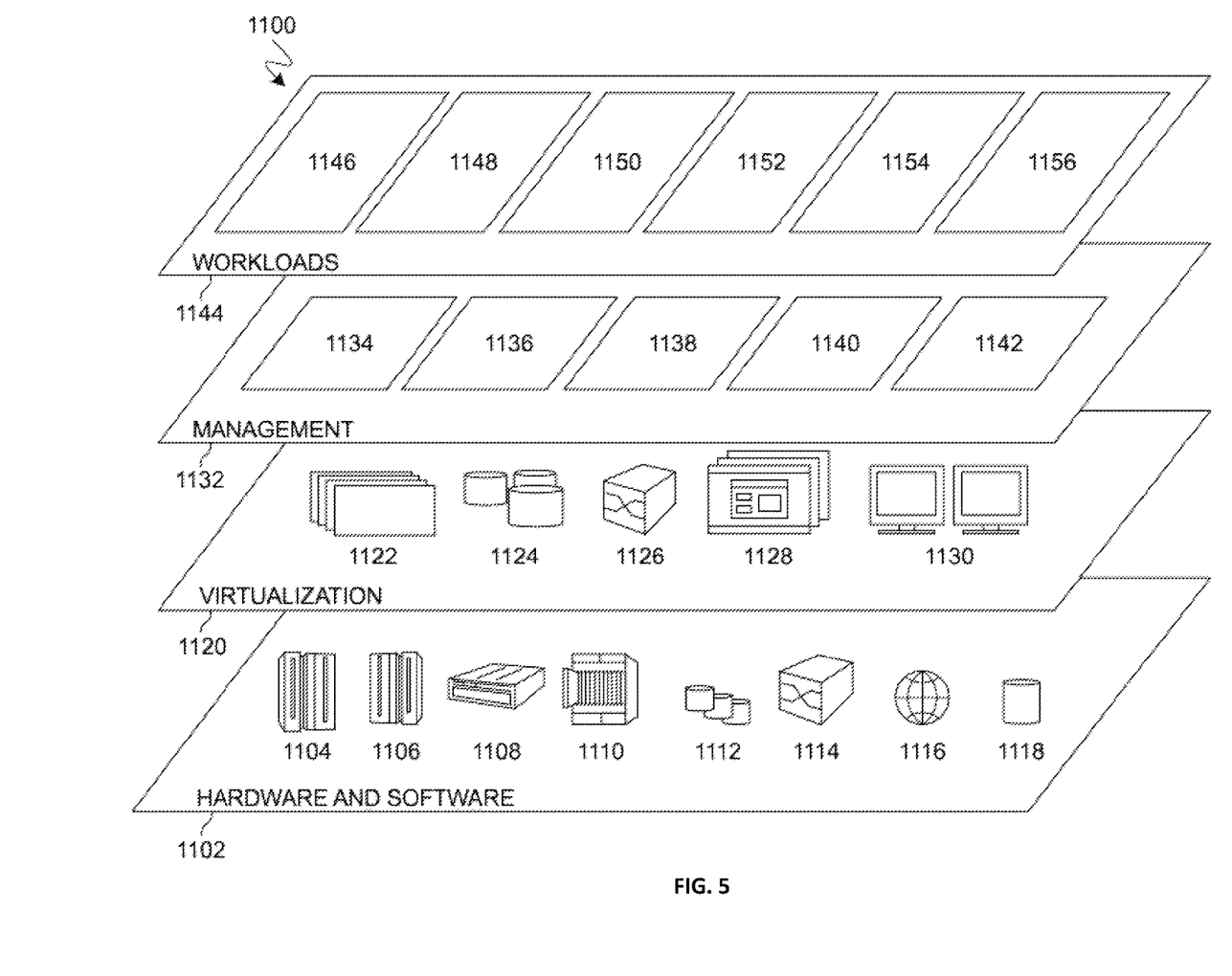
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and automated mutant gene extraction 1156. An automated mutant gene extraction program 110a, 110b provides a way to automate mutant gene extraction.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatically extracting and normalizing at least one mutant gene entity from at least one set of unstructured text, the method comprising:
    extracting the at least one set of unstructured text describing a first entity and a second entity;
    identifying at least one specific first entity and at least one specific second entity described in the extracted at least one set of unstructured text, wherein the at least one specific first entity is normalized, by named entity resolution, into at least one first unified representation in natural language and the at least one specific second entity is normalized, by named entity resolution, into at least one second unified representation in natural language;
    associating the identified at least one normalized specific first entity with the corresponding identified at least one normalized specific second entity;
    creating the at least one mutant gene entity by consolidating at least one set of data associated with the associated at least one normalized specific first entity with the corresponding associated at least one normalized specific second entity;
    identifying at least one semantic relationship between the created at least one mutant gene entity and one or more third entities; and
    storing the consolidated at least one set of data associated with the associated at least one normalized specific first entity and the associated at least one normalized specific second entity, the identified at least one semantic relationship, and the created at least one mutant gene entity in an annotation storage database.

2. The method of claim 1, further comprising:
    retrieving at least one document from a documents database, wherein the retrieved at least one document includes at least one set of unstructured text.

3. The method of claim 2, further comprising:
    parsing through the retrieved at least one document; and
    identifying at least one set of unstructured text describing the first entity and the second entity.

4. The method of claim 1 in which the first entity comprises a mutation.

5. The method of claim 1 in which the second entity comprises a gene.

6. The method of claim 1 in which the one or more third entities comprise of at least one of the following:
    (i) a disease; and
    (ii) a drug.

7. The method of claim 1, wherein identifying at least one semantic relationship between the created at least one mutant gene entity and one or more third entities, further comprises:
    analyzing the extracted at least one set of unstructured text and at least one set of surrounding unstructured text associated with the extracted at least one set of unstructured text; and
    determining at least one semantic relationship of importance between the created at least one mutant gene entity and one or more third entities.

8. The method of claim 1, wherein associating the identified at least one normalized specific first entity with the corresponding identified at least one normalized specific second entity, further comprises:
    analyzing the identified at least one normalized specific first entity and the identified at least one normalized specific second entity from the extracted at least one unstructured text; and
    determining that the analyzed at least one normalized specific first entity and the analyzed at least one normalized specific second entity are related.

9. The method of claim 1, further comprising:
    generating a searchable object associated with the created at least one mutant gene entity; and
    searching, by a user, for the generated searchable object associated with the created at least one mutant gene entity in the annotation storage database.

10. A computer system for automatically extracting and normalizing at least one mutant gene entity from at least one set of unstructured text, comprising:
    one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
    extracting the at least one set of unstructured text describing a first entity and a second entity;
    identifying at least one specific first entity and at least one specific second entity described in the extracted at least one set of unstructured text, wherein the at least one specific first entity is normalized, by named entity resolution, into at least one first unified representation in natural language and the at least one specific second entity is normalized, by named entity resolution, into at least one second unified representation in natural language;
    associating the identified at least one normalized specific first entity with the corresponding identified at least one normalized specific second entity;
    creating the at least one mutant gene entity by consolidating at least one set of data associated with the associated at least one normalized specific first entity with the corresponding associated at least one normalized specific second entity;
    identifying at least one semantic relationship between the created at least one mutant gene entity and one or more third entities; and
    storing the consolidated at least one set of data associated with the associated at least one normalized specific first entity and the associated at least one normalized specific second entity, the identified at least one semantic relationship, and the created at least one mutant gene entity in an annotation storage database.

11. The computer system of claim 10, further comprising:
retrieving at least one document from a documents database, wherein the retrieved at least one document includes at least one set of unstructured text.

12. The computer system of claim 11, further comprising:
parsing through the retrieved at least one document; and
identifying at least one set of unstructured text describing the first entity and the second entity.

13. The computer system of claim 10 in which the first entity comprises a mutation.

14. The computer system of claim 10 in which the second entity comprises a gene.

15. The computer system of claim 10 in which the one or more third entities comprise of at least one of the following:
(i) a disease; and
(ii) a drug.

16. The computer system of claim 10, wherein identifying at least one semantic relationship between the created at least one mutant gene entity and one or more third entities, further comprises:
analyzing the extracted at least one set of unstructured text and at least one set of surrounding unstructured text associated with the extracted at least one set of unstructured text; and
determining at least one semantic relationship of importance between the created at least one mutant gene entity and one or more third entities.

17. The computer system of claim 10, wherein associating the identified at least one normalized specific first entity with the corresponding identified at least one normalized specific second entity, further comprises:
analyzing the identified at least one normalized specific first entity and the identified at least one normalized specific second entity from the extracted at least one unstructured text; and
determining that the analyzed at least one normalized specific first entity and the analyzed at least one normalized specific second entity are related.

18. The computer system of claim 10, further comprising:
generating a searchable object associated with the created at least one mutant gene entity; and
searching, by a user, for the generated searchable object associated with the created at least one mutant gene entity in the annotation storage database.

19. A computer program product for automatically extracting and normalizing at least one mutant gene entity from at least one set of unstructured text, comprising:
one or more computer-readable storage media and program instructions stored on at least one of the one or more tangible storage media, the program instructions executable by a processor to cause the processor to perform a method comprising:
extracting the at least one set of unstructured text describing a first entity and a second entity;
identifying at least one specific first entity and at least one specific second entity described in the extracted at least one set of unstructured text, wherein the at least one specific first entity is normalized, by named entity resolution, into at least one first unified representation in natural language and the at least one specific second entity is normalized, by named entity resolution, into at least one second unified representation in natural language;
associating the identified at least one normalized specific first entity with the corresponding identified at least one normalized specific second entity;
creating the at least one mutant gene entity by consolidating at least one set of data associated with the associated at least one normalized specific first entity with the corresponding associated at least one normalized specific second entity;
identifying at least one semantic relationship between the created at least one mutant gene entity and one or more third entities; and
storing the consolidated at least one set of data associated with the associated at least one normalized specific first entity and the associated at least one normalized specific second entity, the identified at least one semantic relationship, and the created at least one mutant gene entity in an annotation storage database.

20. The computer program product of claim 19, further comprising:
retrieving at least one document from a documents database, wherein the retrieved at least one document includes at least one set of unstructured text.

21. The computer program product of claim 20, further comprising:
parsing through the retrieved at least one document; and
identifying at least one set of unstructured text describing the first entity and the second entity.

22. The computer program product of claim 19 in which the first entity comprises a mutation.

23. The computer program product of claim 19 in which the second entity comprises a gene.

24. The computer program product of claim 19 in which the one or more third entities comprise of at least one of the following:
(i) a disease; and
(ii) a drug.

25. The computer program product of claim 19, wherein associating the identified at least one normalized specific first entity with the corresponding identified at least one normalized specific second entity, further comprises:
analyzing the identified at least one normalized specific first entity and the identified at least one normalized specific second entity from the extracted at least one unstructured text; and
determining that the analyzed at least one normalized specific first entity and the analyzed at least one normalized specific second entity are related.

* * * * *